US008631791B2

(12) United States Patent
Bordewick et al.

(10) Patent No.: US 8,631,791 B2
(45) Date of Patent: *Jan. 21, 2014

(54) APPARATUS AND METHODS FOR ADMINISTRATION OF POSITIVE AIRWAY PRESSURE THERAPIES

(75) Inventors: Steven S. Bordewick, Minneapolis, MN (US); Joseph A. Baser, Lino Lakes, MN (US); Bruce R. Bowman, Eden Prairie, MN (US)

(73) Assignee: Somnetics Global Pte. Ltd., Singapore (SG)

(*) Notice: Subject to any disclaimer, the term of this patent is extended or adjusted under 35 U.S.C. 154(b) by 151 days.

This patent is subject to a terminal disclaimer.

(21) Appl. No.: 13/211,053

(22) Filed: Aug. 16, 2011

(65) Prior Publication Data

US 2012/0000463 A1 Jan. 5, 2012

Related U.S. Application Data

(63) Continuation of application No. 11/786,403, filed on Apr. 10, 2007, now Pat. No. 8,020,557.

(60) Provisional application No. 60/790,671, filed on Apr. 10, 2006.

(51) Int. Cl.
*A61M 11/00* (2006.01)

(52) U.S. Cl.
USPC ............. 128/206.18; 128/207.11; 128/207.17

(58) Field of Classification Search
USPC ............. 128/207.11, 207.13, 207.17, 205.25, 128/206.12, 206.18, 206.21, 206.27, 128/206.28, 201.22–201.24; 2/410, 5, 6.1, 2/6.2, 6.6, 6.8, 417, 418, 421, 422, 424.9
See application file for complete search history.

(56) References Cited

U.S. PATENT DOCUMENTS

| | | |
|---|---|---|
| 3,721,233 A | 3/1973 | Montgomery et al. |
| 4,381,267 A | 4/1983 | Jackson |
| 4,430,995 A | 2/1984 | Hilton |
| 4,493,614 A | 1/1985 | Chu et al. |
| 4,590,951 A | 5/1986 | O'Connor |
| 4,644,947 A | 2/1987 | Whitwam et al. |
| 4,782,832 A | 11/1988 | Trimble et al. |
| 4,944,310 A | 7/1990 | Sullivan |

(Continued)

FOREIGN PATENT DOCUMENTS

| | | |
|---|---|---|
| DE | 102 54 399 A1 | 6/2004 |
| DE | 20 2009 017 541 U1 | 10/2010 |

(Continued)

OTHER PUBLICATIONS

Notice of Rejection Ground dated Jan. 24, 2012 for Japanese Patent Application No. 2009-505491; 15 pgs.

(Continued)

*Primary Examiner* — Steven Douglas
(74) *Attorney, Agent, or Firm* — Mueting, Raasch & Gebhardt, P.A.

(57) ABSTRACT

The present invention provides an apparatus and methods for the administration of positive airway pressure therapies. The apparatus can include a housing, a blower and a mask. The housing is configured to be stably secured on the head of a patient. The blower is secured relative to the housing. A mask in fluid communication with the blower is configured to communicate pressurized air produced at least in part by the blower to the airways of a user.

20 Claims, 8 Drawing Sheets

(56) References Cited

U.S. PATENT DOCUMENTS

| | | |
|---|---|---|
| 4,957,107 A | 9/1990 | Sipin |
| 5,054,484 A | 10/1991 | Hebeler, Jr. |
| 5,104,430 A | 4/1992 | Her-Mou |
| 5,237,987 A | 8/1993 | Anderson et al. |
| 5,349,946 A | 9/1994 | McComb |
| 5,394,870 A | 3/1995 | Johansson |
| RE35,339 E | 10/1996 | Rapoport |
| 5,657,752 A | 8/1997 | Landis et al. |
| 5,687,715 A | 11/1997 | Landis et al. |
| 5,769,071 A | 6/1998 | Turnbull |
| 5,937,855 A | 8/1999 | Zdrojkowski et al. |
| 5,954,050 A | 9/1999 | Christopher |
| 6,213,119 B1 | 4/2001 | Brydon et al. |
| 6,302,105 B1 | 10/2001 | Wickham et al. |
| 6,435,180 B1 | 8/2002 | Hewson et al. |
| 6,435,184 B1 | 8/2002 | Ho |
| 6,516,802 B2 | 2/2003 | Hansen et al. |
| 6,520,182 B1 | 2/2003 | Gunaratnam |
| 6,532,960 B1 | 3/2003 | Yurko |
| 6,532,961 B1 | 3/2003 | Kwok et al. |
| 6,626,177 B1 | 9/2003 | Ziaee |
| 6,634,864 B1 | 10/2003 | Young et al. |
| 6,679,265 B2 | 1/2004 | Strickland et al. |
| 6,694,978 B1 | 2/2004 | Bennarsten |
| 6,711,748 B2 | 3/2004 | Paris et al. |
| 6,715,739 B2 | 4/2004 | Mulvaney et al. |
| 6,823,869 B2 | 11/2004 | Raje et al. |
| 6,854,464 B2 | 2/2005 | Mukaiyama et al. |
| 6,854,465 B2 | 2/2005 | Bordewick et al. |
| 6,895,962 B2 | 5/2005 | Kullik et al. |
| 7,069,932 B2 | 7/2006 | Eaton et al. |
| 7,089,941 B2 | 8/2006 | Bordewick et al. |
| 7,096,864 B1 | 8/2006 | Mayer et al. |
| 7,156,090 B2 | 1/2007 | Nomori |
| 7,195,014 B2 | 3/2007 | Hoffman |
| D555,235 S | 11/2007 | Korkowski et al. |
| 7,318,437 B2 | 1/2008 | Gunaratnam et al. |
| 7,357,136 B2 | 4/2008 | Ho et al. |
| 7,370,652 B2 | 5/2008 | Matula, Jr. et al. |
| 7,487,778 B2 | 2/2009 | Freitag |
| 7,516,743 B2 | 4/2009 | Hoffman |
| 7,525,663 B2 | 4/2009 | Kwok et al. |
| 7,588,033 B2 | 9/2009 | Wondka |
| 7,665,465 B2 | 2/2010 | Radney |
| 7,779,832 B1 | 8/2010 | Ho |
| 7,789,194 B2 | 9/2010 | Lathrop et al. |
| 7,814,911 B2 | 10/2010 | Bordewick et al. |
| 7,845,353 B2 | 12/2010 | Bordewick et al. |
| 7,874,293 B2 | 1/2011 | Gunaratnam et al. |
| 7,913,692 B2 | 3/2011 | Kwok |
| 7,931,023 B2 | 4/2011 | Berthon-Jones et al. |
| 7,931,026 B2 | 4/2011 | Ho et al. |
| 8,020,557 B2 | 9/2011 | Bordewick et al. |
| 8,074,645 B2 | 12/2011 | Bordewick et al. |
| 8,091,553 B2 | 1/2012 | Bordewick et al. |
| 8,327,846 B2 | 12/2012 | Bowditch et al. |
| 8,336,546 B2 | 12/2012 | Bowditch et al. |
| 8,375,944 B2 | 2/2013 | Kwok |
| 8,413,657 B2 | 4/2013 | Amarasinghe et al. |
| 2002/0011248 A1 | 1/2002 | Hansen et al. |
| 2004/0035427 A1 | 2/2004 | Bordewick et al. |
| 2004/0226562 A1 | 11/2004 | Bordewick |
| 2005/0284481 A1 | 12/2005 | Meyer et al. |
| 2006/0096596 A1 | 5/2006 | Occhialini et al. |
| 2006/0231097 A1 | 10/2006 | Dougherty et al. |
| 2006/0231102 A1 | 10/2006 | Bordewick et al. |
| 2006/0237013 A1 | 10/2006 | Kwok |
| 2007/0089743 A1 | 4/2007 | Hoffman |
| 2007/0247009 A1 | 10/2007 | Hoffman et al. |
| 2007/0277827 A1 | 12/2007 | Bordewick |
| 2008/0006275 A1 | 1/2008 | Nickelson et al. |
| 2008/0099017 A1 | 5/2008 | Bordewick et al. |
| 2009/0078255 A1 | 3/2009 | Bowman et al. |
| 2009/0078258 A1 | 3/2009 | Bowman et al. |
| 2010/0018534 A1 | 1/2010 | Veliss et al. |
| 2010/0065054 A1 | 3/2010 | Bowman et al. |
| 2012/0097156 A1 | 4/2012 | Bowman et al. |
| 2012/0167879 A1 | 7/2012 | Bowman et al. |
| 2013/0098359 A1 | 4/2013 | Becker et al. |
| 2013/0133661 A1 | 5/2013 | Kwok |

FOREIGN PATENT DOCUMENTS

| | | |
|---|---|---|
| EP | 0 558 147 A1 | 9/1993 |
| EP | 1 655 052 A2 | 5/2006 |
| EP | 1 655 052 A3 | 7/2006 |
| EP | 1 334 742 B1 | 4/2008 |
| EP | 2 085 106 A1 | 8/2009 |
| JP | 2002-511786 | 4/2002 |
| JP | 2003-235982 | 8/2003 |
| JP | 2006-130320 | 5/2006 |
| JP | 2007-501074 | 1/2007 |
| JP | 2007-506482 | 3/2007 |
| WO | WO 91/19527 A1 | 12/1991 |
| WO | WO 99/21602 A1 | 5/1999 |
| WO | WO 99/47197 A1 | 9/1999 |
| WO | WO 02/085417 A2 | 10/2002 |
| WO | WO 02/085417 A3 | 12/2003 |
| WO | WO 2004/112873 A1 | 12/2004 |
| WO | WO 2005/002655 A1 | 1/2005 |
| WO | WO 2005/013879 A2 | 2/2005 |
| WO | WO 2005/028009 A1 | 3/2005 |
| WO | WO 2006/044120 A2 | 4/2006 |
| WO | WO 2006/050384 A2 | 5/2006 |
| WO | WO 2006/044120 A2 | 8/2006 |
| WO | WO 2006/044120 A3 | 10/2006 |
| WO | WO 2007/149446 A2 | 12/2007 |
| WO | WO 2007/149446 A3 | 2/2008 |
| WO | WO 2010/080709 A1 | 7/2010 |
| WO | WO 2010/096467 A1 | 8/2010 |
| WO | WO 2011/022779 A1 | 3/2011 |

OTHER PUBLICATIONS

Moran, "CPAP outside the box," *HME News*, May 2006; 2 pgs.
International Preliminary Report on Patentability for PCT/US2007/009082 dated Jul. 28, 2008; 6 pgs.
International Search Report for PCT/US2007/009082 dated Oct. 4, 2007; 2 pgs.
Written Opinion of the International Searching Authority for PCT/US2007/009082 dated Oct. 4, 2007; 5 pgs.
Decision to Grant dated May 28, 2013 for Japanese Patent Application No. 2009-505491; 3 pgs.
Notice of Rejection Ground dated Aug. 7, 2012 for Japanese Patent Application No. 2009-505491; 3 pgs.

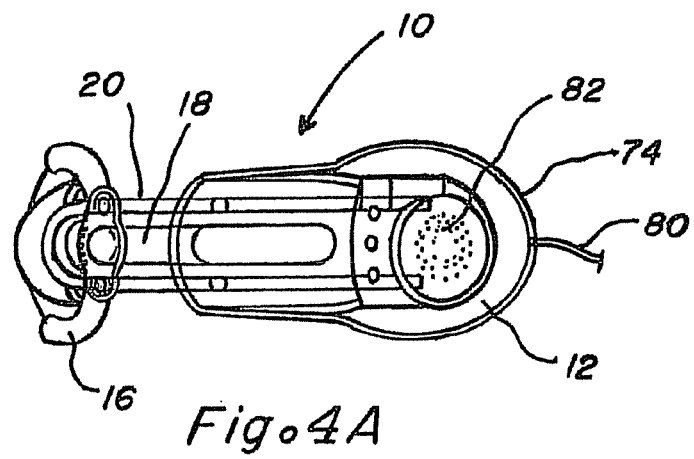
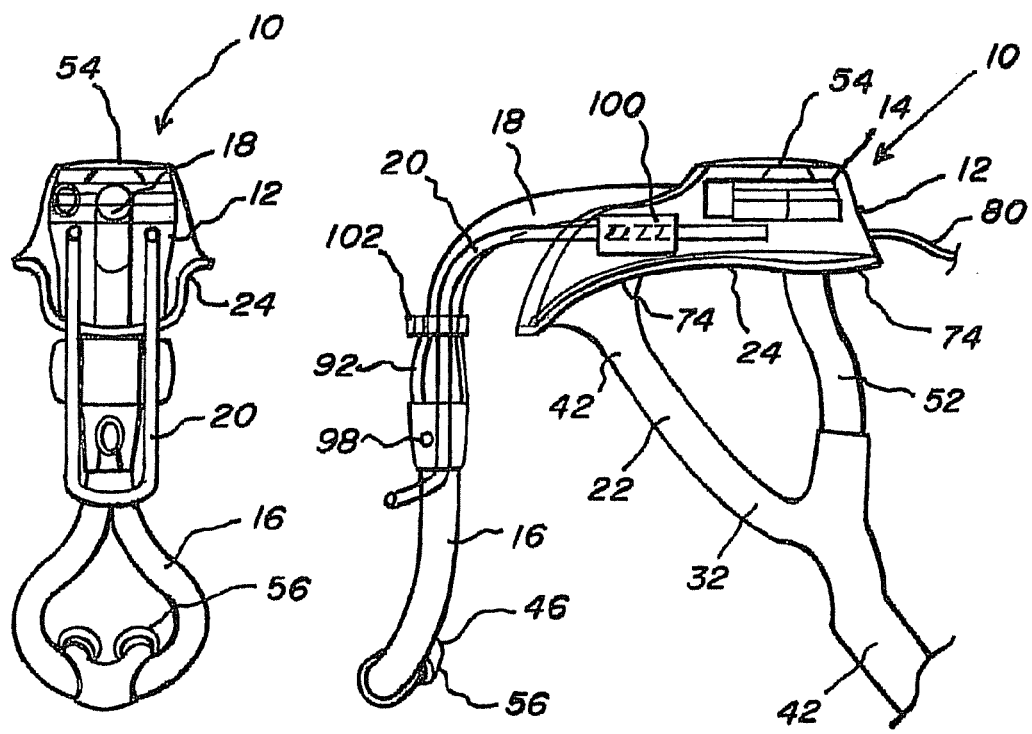
Fig. 4A
Fig. 4B
Fig. 4C

APPARATUS AND METHODS FOR ADMINISTRATION OF POSITIVE AIRWAY PRESSURE THERAPIES

CROSS-REFERENCE TO RELATED APPLICATIONS

This is a continuation application of U.S. patent application Ser. No. 11/786,403, filed Apr. 10, 2007, which claims the benefit under 35 U.S.C. §119(e) of U.S. Provisional Application Ser. No. 60/790,671, filed on Apr. 10, 2006, the disclosures of which are both hereby incorporated by reference in their respective entireties.

BACKGROUND OF THE INVENTION

1. Field of the Invention

The present inventions relate generally to respiratory therapy and, more particularly, to apparatus and methods providing positive airway pressure therapy.

2. Background of the Related Art

Positive airway pressure therapies are frequently used in the treatment of sleep apnea, chronic pulmonary obstruction and snoring. These therapies typically pressurize the airways of a user to a pressure in the range of 4-20 cm water. Depending upon the particular therapy, a variable or a constant pressure therapy may be administered to the user to reduce or eliminate occlusions that dictated the use of the therapy.

Typically, the therapeutic devices used to provide the positive airway pressure therapy include at least a blower unit, an elongated hose, and a mask. The blower unit is frequently a relatively large component which rests on a bedside table or the floor adjacent to the bed. The blower typically includes a fan or turbine, a motor, and associated controls. Accordingly, the blower is typically heavy and, while operating, can be relatively noisy given its intended use during sleep. The elongated hose is typically configured to span a distance between at least a user's head and the location at which the blower unit resides, typically a night-stand or the floor. The elongated hose typically communicates pressurized air or other gasses between the blower and the mask. Accordingly, the first end of the elongated tube is typically connected to an outlet on the blower and the second end of the elongated tube is typically connected to the mask. The mask is generally configured to be secured relative to a user's head and to communicate pressurized air into the airways of the user during sleep.

The blowers can be noisy. The noise can disrupt sleep of a user or others in close proximity. Therefore, a need exists for apparatus and methods to reduce the noise levels created by positive airway pressure devices.

In many variations, the face or the head of a user is tethered by a hose to a remotely positioned blower. The hoses associated with typical positive airway pressure therapy device are around six feet long. The length of the hoses is typically fixed. The placement of the blower device may be limited by the hose and its connection point on the outlet of the blower as well as the air inlet position on the mask. The length can be a nuisance for storage. Further, due to placement of the blower relative to a user, the fixed lengths are frequently either too long or too short generating slack or tension, respectively, between a remotely positioned blower and the user's head. Portions of the length of hose may become entangled in the bedding and inadvertently move the blower or displace the mask. Either condition may limit a user's ability to freely change head and body positions during sleep. The inability to freely change head and body positions during sleep can disrupt the sleep of a user. Further, the changing body positions creating tension or compression in the tube can torque the mask and cause leaks which may adversely affect the administration of the therapy. Therefore, a need exists for apparatus and methods that do not inhibit the ability to freely change head and body positions during sleep during the administration of a positive airway pressure therapy.

In addition, an excessive length of hose can create a potential safety hazard due to a possibility of it becoming wrapped around a user's neck or the hose being inadvertently entangled with another individual next to or in the same bed. Therefore, a need exists for apparatus and methods that reduce the length of hosing necessary for administration of a positive airway pressure therapy.

In addition, sound from the blower that may travel through the hose can be disruptive to a user or another individual next to or in the same bed. Therefore, a need exists for apparatus and methods that may mitigate the noise propagated by the hose.

The bulk and noise of typical therapeutic devices as well as the bulk of the hose reduce the portability of the apparatus and can make it generally difficult to transport the prior therapeutic devices when traveling. Further problems can be created by divergent placement locations for the blower relative to the bed which may be presented in various sleeping accommodations which may result in a hose that is too long or too short. Therefore, a need exists for apparatus and methods that may reduce the size of the positive airway pressure apparatus and provide improved portability.

SUMMARY OF THE INVENTION

Apparatus and methods in accordance with the present invention may resolve one or more of the needs and shortcomings discussed above and will provide additional improvements and advantages as will be recognized by those skilled in the art upon review of the present disclosure.

Apparatus in accordance with aspects of the present inventions may include a housing, a blower and a mask. The housing may define a lower housing surface. At least a portion of the lower housing surface can be adapted to be secured on the head of a user. The housing can be configured to enclose at least a portion of a blower. The blower may be enclosed in a housing interior. The housing can include a base and a cover. The housing can include at least a base. The blower can be secured to the base and the base can define the lower surface configured to conform to the head of a user. The base may be configured as a head mount platform module. The housing may include a blower module removably secured to the head mount platform module. The housing may also include a blower module and a humidifier module. The blower module and the humidifier module may be removably secured to the head mount platform module. The housing may define a housing interior and a sound deadening material positioned within at least a portion of the housing interior. The blower may be configured for the administration of positive airway pressure therapy. The blower defines at least a blower inlet and a blower outlet. The blower can be secured to the housing so that the blower can be retained on the head of a user. A humidifier may also be secured to the housing so that the humidifier can be retained on the head of the user. The mask can be secured in a position relative to the housing. The mask can define a mask inlet, a mask passage and a mask outlet. The mask inlet may be in fluid communication with the blower outlet of the blower. The mask can be configured to sealably engage the user over an airway of the user and to communicate pressurized air to the airway in administration of a positive airway pressure therapy. A mount may also be provided with the mount configured to secure the housing relative to a head of a user. An air delivery tube may be secured to at least the mask. The air delivery tube can define at least a portion of a pressurized air passage extending between the blower and the mask. The mount can include at least one support band. The support band may include at least one chin strap. A control unit can be provided in communication with a noise cancellation speaker. The control unit may be configured to provide an output to the noise cancellation speaker to produce a waveform to at least mitigate a sound produced by at least the blower. A microphone may also be provided in communication with the control unit. The microphone can be configured to provide an output indicative of the sound produced by at least the blower. When a microphone is provided, the control unit can be configured to process the output from the microphone to produce the output to the noise cancellation speaker to produce the waveform to at least mitigate the sound produced by at least the blower.

Methods in accordance with aspects of the present inventions may include securing a blower on a head of a user; securing a mask over an air passageway of the user; and providing a positive airway pressure therapy to the airway of the user. The methods may also or alternatively include producing a waveform to at least mitigate a sound produced by a blower.

Other features and advantages of the invention will become apparent from the following detailed description, and from the claims.

BRIEF DESCRIPTION OF THE FIGURES

FIG. 4A a top view of an embodiment of a positive airway pressure apparatus in accordance with aspects of the present inventions;

FIG. 4B a front view of a positive airway pressure apparatus similar to the embodiment of FIG. 4A in accordance with aspects of the present inventions;

FIG. 4C a side view of an embodiment of a positive airway pressure apparatus similar to the embodiment of FIGS. 4A and 4B in accordance with aspects of the present inventions;

Figure 1:
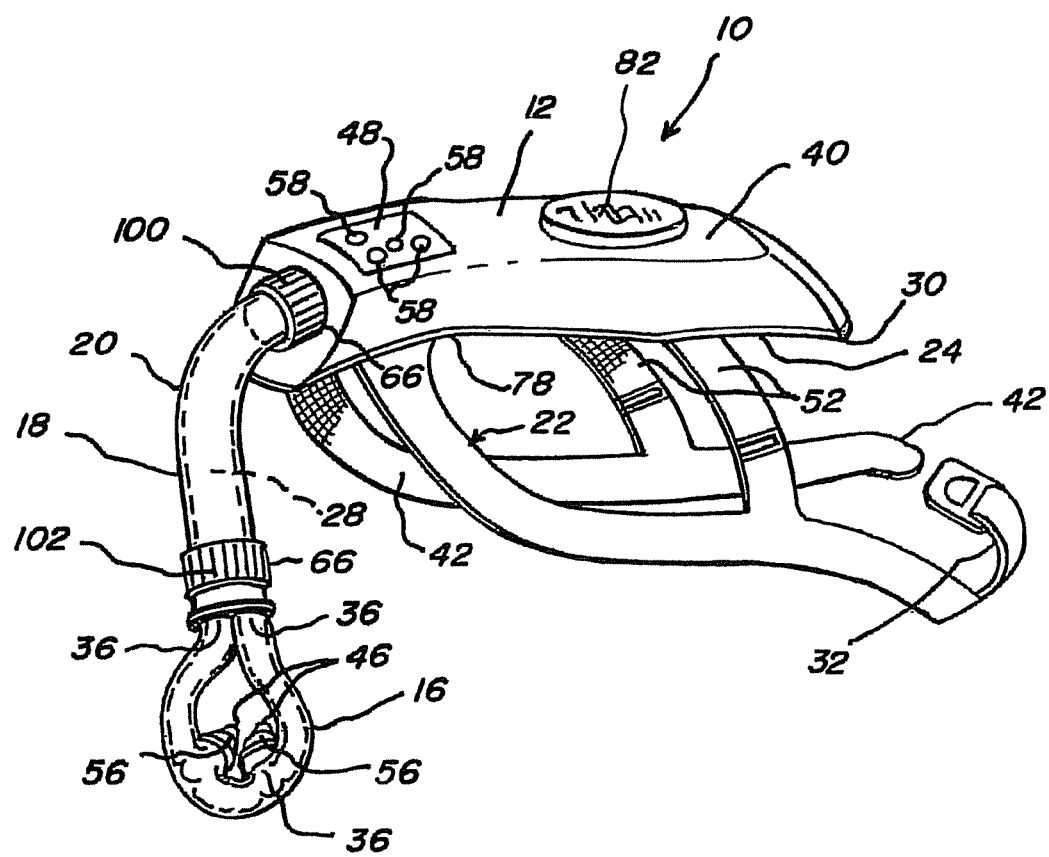
FIG. 1 illustrates a perspective view of an embodiment of a positive airway pressure apparatus in accordance with aspects of the present inventions.

All Figures are illustrated for ease of explanation of the basic teachings of the present invention only; the extensions of the Figures with respect to number, position, relationship and dimensions of the parts to form the embodiment will be explained or will be within the skill of the art after the following description has been read and understood. Further, the exact dimensions and dimensional proportions to conform to specific force, weight, strength, flow and similar requirements will likewise be within the skill of the art after the following description has been read and understood.

Where used in various Figures of the drawings, the same numerals designate the same or similar parts. Furthermore, when the terms "top," "bottom," "right," "left," "forward," "rear," "first," "second," "inside," "outside," and similar terms are used, the terms should be understood to reference only the structure shown in the drawings and utilized only to facilitate describing the illustrated embodiments. Similarly, when "medial," "lateral," "superior," "inferior" and similar terms are used, particularly when used to describe relative positions, the terms should be understood to reference the structures shown in the drawings as they will typically be implemented by a user wearing the apparatus in accordance with the present inventions.

DETAILED DESCRIPTION OF THE INVENTION

The present inventions provide positive airway pressure apparatus 10 and associated methods for use in conjunction with positive airway pressure therapies. The figures generally illustrate embodiments of positive airway pressure apparatus 10 including aspects of the present inventions. The particular exemplary embodiments of the positive airway pressure apparatus 10 illustrated in the figures have been chosen for ease of explanation and understanding of various aspects of the present inventions. These illustrated embodiments are not meant to limit the scope of coverage but instead to assist in understanding the context of the language used in this specification and the appended claims. Accordingly, variations of positive airway pressure apparatus 10 for use in positive airway pressure therapies that are different from the illustrated embodiments may be encompassed by the appended claims.

Positive airway pressure apparatus 10 in accordance with aspects of the present inventions are generally configured to be secured relative to the head of a user. The positive airway pressure apparatus 10 are configured to position a mask 16 in communication with the airways of a user to provide pressurized air and/or other gases for positive airway pressure therapy. The therapy may provide constant or variable positive airway pressure to the airways of the user as will be recognized by those skilled in the art upon review of the present disclosure.

The positive airway pressure apparatus 10 in accordance with the present inventions include at least a housing 12, a blower 14 and a mask 16. The housing 12 is generally configured to be secured to the head of a user. In certain aspects, the housing 12 may be configured to be secured on one or both of the crown or the forehead of a user. The blower 14 is secured to the housing 12. The blower 14 is typically secured on or in the housing 12. The blower 14 is generally configured to generate a flow of pressurized air and/or other gas for a user's respiratory therapy. The flow of pressurized air is directed through an air delivery passage 28 to the mask 16. The air delivery passage 28 may be defined by the housing 12 and/or an air delivery tube 18. The mask 16 is generally configured to communicate pressurized air to the airways of a user. The mask 16 may be particularly configured to direct air from the air delivery passage 28 into airways of a patient. Typically, the mask 16 is secure over one or both of the mouth and the nose of a user. A seal or other portion of the mask is typically configured to sealingly engage an aspect of the patient's anatomy such that a positive airway pressure therapy may be administered to a user.

The mask 16 generally defines a mask passage 26 having a mask inlet 36, and one or more mask outlets 46. The one or more mask outlets 46 may include one or more mask seals 56 to sealingly engage aspects of the user's anatomy. In certain aspects, the mask seals 56 may be removable and interchangeable to permit proper fitment and/or replacement of worn mask seals 56. In certain aspects, the mask outlet 46 and the seals 56 may be formed as a unitary structure. The mask passage 26 is defined by the mask 16 and is configured to receive pressurized air from the blower 14 through the mask inlet 36. The mask inlet 36 may communicate with the air delivery passage 28 to receive pressurized air from the blower 14. In certain aspects, the mask 16 may be secured to the housing 12 and/or the air delivery tube 18 to permit communication of air from air delivery passage 28 into mask passage 26. In certain aspects, portions of mask 16 and/or mask inlet 36 may be configured to receive an air delivery tube 18 or to be received by an air delivery tube 18. The mask outlet 46 is defined by the mask body and/or the seal(s) 56 of the mask 16. The mask outlet 46 is configured to communicate air from the passage 26 to the airway of a user. The seal 56 or seals 56 are typically configured to abut a portion of the face of a user to permit pressurized air to be communicated through the passage 26 to the airway of a user from the mask outlet 46.

Portions of mask 16 may be formed from a rigid or substantially rigid material while other portions are formed from a compliant material as will be recognized by those skilled in the art upon review of the present disclosure. Various stiffening or shaping wires may be integrated into the mask 16 or secured to the mask 16. The wires may be configured to assist in the fitment of the mask 16 or otherwise as will be recognized by those skilled in the art.

The mask 16 may be configured as a face mask, a nose mask, a pair of nares seals, a mouth piece, or otherwise as will be recognized by those skilled in the art upon review of the present disclosure. The mask 16 is secured to the housing 12. In certain aspects, the mask 16 may be secured relative to housing 12. Depending on the particular configuration of the positive airway pressure apparatus 10, the mask 16 may exert a force about a moment arm extending from the housing 12, may be held in tension between aspects of the users face and the housing 12, may exert a combination of such forces, or may otherwise contact a user's anatomy to permit adequate sealing for administration of a positive airway pressure therapy. One or more mounts 22 may be secured to the mask 16. The mask 16 may be biased against a user's anatomy with the one or more mounts 22. In certain aspects, the mounts 22 may be configured as one or more bands 32 to sealably secure the mask 16 over at least an aspect of the user's anatomy. In other aspects, the mask 16 may be sealably secured over at least an aspect of the face of a user by one or more of the delivery tube 18, a mask support 20 and the housing 12.

Figure 3:
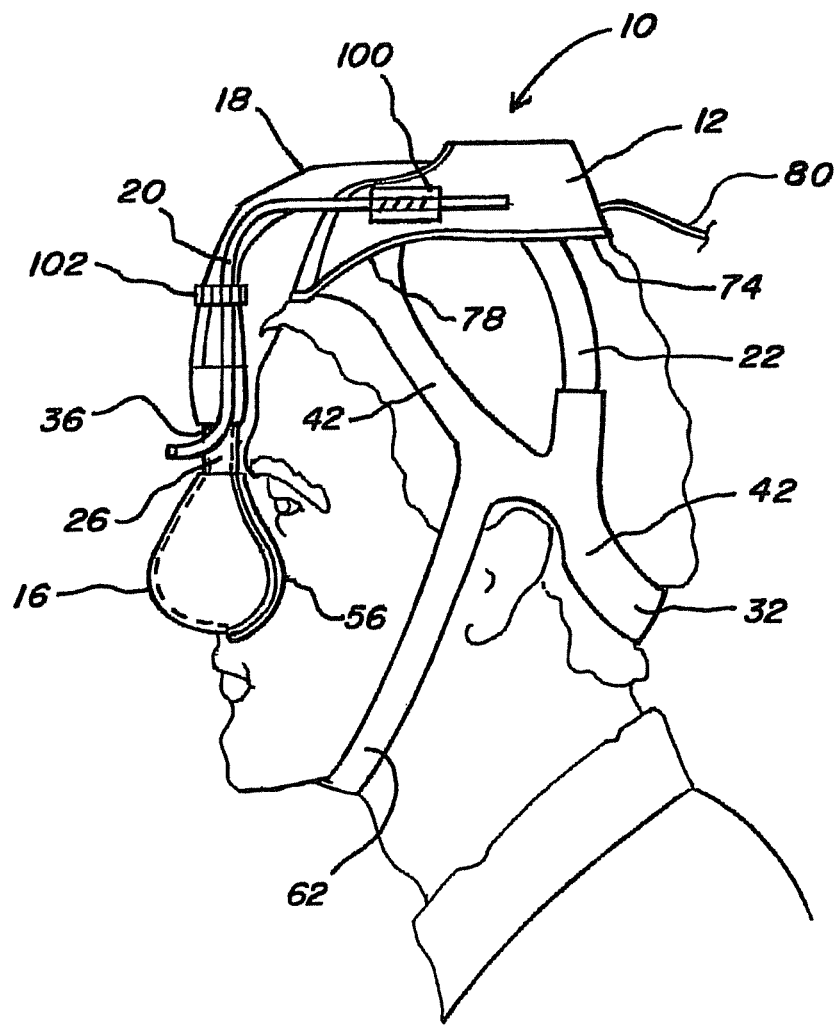
FIG. 3 illustrates a side view of an embodiment of another positive airway pressure apparatus in accordance with aspects of the present inventions secured to the head of a user.

As generally illustrated in the Figures, masks 16 may be cantilevered against a user's face or other portions of the user's anatomy from the housing 12. The mask 16 may include one or more supports 20 to permit the mask 16 to exert sufficient force against the face or portion thereof of the user to seal the mask 16 against the user to permit the administration of a positive airway pressure therapy. In certain aspects, the air delivery tube 18 or aspects of air delivery tube 18 may function as the mask support 20 as is generally illustrated in FIGS. 1 and 3. In other aspects, the mask 16 may be secured directly to the housing 12, may be secured to the housing 12 with a mask support 20, or may be otherwise secured as will be recognized by those skilled in the art upon review of the present disclosure.

The housing 12 is generally configured to be stably secured to the head of a user. One or more mounts 22 may be provided to secure the housing 12 to the user's head. The structure of the housing 12 may be unitary or composite in structure. When composite in structure, the housing 12 may include a base 30 and a cover 40. The base 30 and the cover 40 may be integral, inter-lockable, hingably attached to one another or otherwise securable to one another. In certain aspects, portions of the base 30 and the cover 40 are integrally formed as two components, such as left and right halves, which may be secured to one another to form the housing 12. In other aspects, the base 30 and the cover 40 are formed as two components, such as top and bottom halves, which may be secured to one another to form the housing 12. Typically, the housing 12 is configured to be secured over the top of the head of a user, over aspects of the top of the head and forehead of a user, or over the forehead of a user. A lower housing surface 24 of the housing 12 may be shaped to generally conform to the portion of the head to which the housing 12 is intended to be positioned and secured with the mount 22. Accordingly, the lower housing surface 24 may be flat, may include one or more curves 78 or may be otherwise shaped or configured as will be recognized by those skilled in the art upon review of the present disclosure. In certain aspects, at least a portion of the lower housing surface 24 may be defined by the base 30.

In one aspect, the housing 12 may include a base 30 to which the blower 14 and other components are secured and a cover 40 which is securable over the base 30 to define a housing interior 72. The base 30 may be formed from a rigid or a flexible material. When flexible or otherwise configured as will be recognized by those skilled in the art, the base 30 or other structure defining the lower housing surface 24 of the housing 12 may be configured to be shaped to the contours of the head of a user. When rigid, semi-rigid or otherwise configured as will be recognized by those skilled in the art, the base 30 or other structure defining the lower housing surface 24 of the housing 12 may be configured with a curve 78 or one or more flexible sections or hinges to permit the lower housing surface 24 to be more closely contoured to the shape of the head of a user. Other or alternative structures and materials may be provided to permit the housing 12 to be comfortably and securely held on the head of a user as will be recognized by those skilled in the art upon review of the present disclosure.

The housing 12 may be further configured to provide a stable structure to which the mask 16 is mounted or secured either directly or indirectly. Portions of the housing 12 may define an air delivery passage 28 to communicate pressurized air from the blower 14 to the mask passage 26 of the mask 16. In certain aspects, a portion of the air delivery passage 28 may be formed by the housing 12 and a portion may be formed by the air delivery tube 18. In other aspects, the entirety of air delivery passage 28 may be formed by the air delivery tube 18 or the housing 12.

The housing 12 may include a pad 74 secured to at least a portion of the lower surface 24 of the housing 12. The pad 74 may conform to the shape of the lower surface 24 of the housing 12. In certain aspects, the pad 74 may provide a cushion between the housing 12 and the head of a user. In other aspects, the pad 74 may function as a structural member which is connected to or integral with the mount 22 to receive a force exerted by the mount 22. In other aspects, the pad 74 may function both as a structural member and a cushion. In other aspects, the pad 74 may be made with a breathable material to reduce moisture from sweating. In yet other aspects, the pad 74 may function as a frictional element which may assist in stabilizing the positive airway pressure apparatus 10 in a desired position on the head of a user. Those skilled in the art may recognize additional functions for a pad 74 upon review of the present disclosure.

The blower 14 is secured to the housing 12. The housing 12 generally provides a stable structure to which at least a blower 14 is mounted and permits the blower 14 to be secured in a position relative to the head of a user. In one aspect, at least a portion of the blower 14 is secured to and enclosed within the housing 12. In this aspect, an inner surface of the housing 12 may define a housing interior 72, typically in the form of a cavity or chamber, in which the blower 14 is secured. The housing 12 may be further configured to secure and/or enclose at least a portion of other components of the positive airway pressure apparatus 10 such as, for example, a battery 60, a humidifier 90, a control unit 38 among other components when present.

The air delivery tube 18, when present, is generally configured to communicate air from the blower 14 or the portion of the air delivery passage 28 defined by housing 12 to the mask passage 26 of the mask 16. The air delivery tube 18 may be in the form of a hose. Typically, the air delivery tube 18 will be formed from a flexible ribbed hose. In other aspects, the air delivery tube 18 may be rigid or semi-rigid. When rigid or semi-rigid, the air delivery tube 18 may at least in part maintain alignment and seal of the mask 16. In certain aspects, the air delivery tube 18 may include various damping, flexible, rotatable, bendable and/or torquable elements to reduce the forces transmitted between the housing 12 and mask 16 as a user sleeps. An opening at a first end of the air delivery tube 18 is generally configured to communicate with the source of pressurized air. An opening at the second end of the air delivery tube 18 is generally configured to communicate pressurized air to the passage 26 of a mask 16.

One or more mounts 22 may be provided to secure the housing 12 relative to the head of a user. The mounting(s) 22 may be in the form of a flexible cap, one or more rigid or semi rigid members, one or more bands 32 or various other structures alone or in combination. Those skilled in the art will recognize a wide range of additional available structures to secure the positive airway pressure apparatus 10 to the head of a user.

As generally illustrated throughout the Figures, the mount(s) 22 may include one or more support bands 32 to secure the housing 12 relative to the head of a user. The support bands 32 and the housing 12 may be generally configured to secure the housing 12 in a medial position on the head of a user as illustrated.

The support bands 32 are typically in the form of elongated members that are configured to exert sufficient tension to retain the housing 12 on the head of a user and maintain the mask 16 in substantially sealed communication with the airways of a user as the user sleeps. In certain aspects, the support bands 32 are configured as flattened straps to comfortably distribute a force over their surface area. The bands 32 may be formed from one or more stretchable elastic materials, substantially unstretchable material, or other materials as will be recognized by those skilled in the art upon review of the present disclosure. The support bands 32 may be integrally formed or interconnected with one another and the housing 12 by a variety of mechanical linkages. The one or more of the support bands 32 may have adjustable lengths to permit the proper fitting of the positive airway pressure apparatus 10 to a user. The support bands 32 may incorporate various buckles, snaps, hook and loop type fasteners, such as that sold under the trade name Velcro®, or other components to link and/or permit relative adjustment of the support bands 32. Various aspects of the support bands 32 may be adjustable by a user. These aspects may include length, relative positions or other aspects as will be recognized by those skilled in the art upon review of the present disclosure.

As shown in the illustrated exemplary embodiments, the support bands 32 may include one or more of a circumferential band 42, a first lateral stabilizing band 52, a second lateral stabilizing band 52, and a chin band 62. The support bands 32 are generally configured to secure the relative position of the housing 12 on the head of a user. One or more of the support bands 32 may be secured to the housing 12. The circumferential band 42 may be configured to extend around at least a portion of the head of a user. A portion of the housing 12 may be secured to the circumferential band 42. The first and second lateral stabilizing bands 52 generally extend between the circumferential band 42 and the housing 12.

The blower 14 typically includes an air pressurizing assembly 34 having a blower motor 44. The blower 14 may be particularly configured for noise abatement and vibration reduction. In certain embodiments, the blower may include an air bearing for noise abatement and vibration reduction as well as wear characteristics. As such, the blower 14 may be particularly configured to reduce vibration, and noise as will be recognized by those skilled in the art upon review of the present disclosure. The air pressurizing assembly 34 typically includes a blower inlet 54 to receive air and a blower outlet 64 to direct pressurized air toward the air delivery passage 28. The blower 14 is generally adapted to generate and deliver pressurized air to the blower outlet 64 of the air pressurizing assembly 34. The blower 14 may also include one or more noise absorption baffles and/or resonators. In certain aspects, a Helmholtz type resonator 68 may be in fluid communication with the blower outlet 64. As illustrated, the Helmholtz type resonator may be secured adjacent to the blower outlet 64. In other aspects, the Helmholtz type resonator 68 may be secured to the blower inlet 54 or otherwise be positioned in communication with the pressurized air passage 28. The air pressurizing assembly 34 may include one or more of various fans, turbines, impellers, pumps, ducts, inlets, conduits, passages, sensors, mufflers, and other components configured to pressurize air as will be recognized by those skilled in the art upon review of the present disclosure. The various fans, turbines, impellers, and/or pumps are typically driven by the blower motor 44. The blower motor 44 may be connected to the air pressurizing assembly 34 directly through a drive shaft or indirectly through one or more, belts, chains, gears, pulleys, shafts or other components as will be recognized by those skilled in the art. In certain aspects, the components of the blower 14 may be selected to reduce or eliminate noise and vibration. The components of the blower 14 may also be selected and configured to reduce the overall mass of the positive airway pressure apparatus.

A power source 80 is typically required to power the components of the positive airway pressure apparatus 10. The power source 80 may be a household electrical outlet providing alternating (AC) current or may be a battery 60. The power source 80 may be remotely locatable or may be secured to the housing 12. In certain aspects, a direct current (DC) converter 108 may be provided to appropriately convert an alternating current of an outlet to a direct current which is typically utilized by the components of the positive airway pressure apparatus 10. The DC converter 108 may be positioned at any convenient location on the power supply cord to permit its positioning on adjacent bedside table, under the pillow of the user, on the floor, or elsewhere as will be recognized by those skilled in the art upon review of the present disclosure.

In addition or alternatively, the power source 80 may include a battery 60. The battery 60 may be directly connected to the DC converter 108 while the converter 108 is connected to a household electrical outlet and function as a backup power source in the event of a power outage or may be configured to be the sole source of power for the components of the positive airway pressure apparatus 10. When connected to a household electrical outlet, the battery 60 may be maintained in a fully charged condition until a power outage. If the external power source is not provided or fails, the battery 60 may power the blower 14 and other components until power from the primary external power source 80 is regained or the battery 60 has discharged. When securable to the housing 12, the battery 60 is typically removable from the housing 12 for purposes of recharging or replacement. In one aspect, the battery 60 may include at least one interlock 70 to removably secure the battery 60 from the housing 12. In other aspects, the battery 60 may be remotely located and electrically connected to the components of the positive airway pressure apparatus 10 by a cable. In this configuration, electrical connectors are typically provided on the cable and the positive airway pressure apparatus 10 to communicate electricity to the various components of the positive airway pressure apparatus 10.

A humidifier 90 may be provided to communicate moisture into the pressurize air passing through the air delivery passage 28 to humidify the pressurized air delivered to the user. The moisture provided by the humidifier 90 may be in the form of water vapor, liquid water droplets, mist, micro-droplets, fog, or various combinations of liquid water and water vapor. The pressurized air may be humidified for therapy, comfort, or other reasons, as will be recognized by those skilled in the art upon review of the present disclosure. The humidifier 90 may be secured to or within the housing 12. The humidifier 90 generally includes at least a humidifier reservoir 92 and, in certain configurations, a humidifier pump 94 or humidifier heater 96. The humidifier 90 may add moisture and/or therapeutic agents to the air delivered to the user. As generally illustrated throughout the Figures for exemplary purposes, the humidifier 90 includes a humidifier reservoir 92 secured within the housing 12. A fill tube accessible by a user may be provided on the housing 12 for filling the humidifier reservoir 92 without removing portions of the housing 12 or humidifier reservoir 92. The humidifier reservoir 92 typically contains water and/or therapeutic agents to be introduced as part of the user's therapy.

Depending on the particular configuration, the humidifier reservoir 92 may be in fluid communication with a humidification port 98 to introduce moisture from the humidifier reservoir 92 into the pressurized air produced by the blower 14. The humidifier reservoir 92 may be resident on the housing 12 or may be positioned remote from the housing 12 as will be recognized by those skilled in art upon review of the present disclosure. The humidification port 98 may be anywhere along mask passage 26, the air delivery passage 28, and/or within aspects of the air pressurizing assembly 34. In some aspects, there may be a plurality of humidification ports 98 to introduce moisture at various points along the mask passage 26, the air delivery passage 28, and/or within aspects of the air pressurizing assembly 34. In some aspects, the humidifier reservoir 92 may include baffles, absorbent materials, or other features to inhibit the movement of water within the humidification reservoir.

The humidifier heater 96 may heat the water and/or therapeutic agents in the reservoir 92 to facilitate their introduction into the pressurized air within pressurized air passage 28 and/or for the comfort or therapy of the user. In certain aspects, the humidifier heater 96 may provide a rate of evaporation adequate to humidify the air delivered to the user.

The humidifier pump 94 or a series of humidifier pumps 94 may be provided to introduce the moisture into the pressurized air at the humidification port 98. In certain embodiments, the humidifier heater 96 may additionally or alternatively assist in the introduction of moisture into the pressurized air at the humidification port 98. Further, some configurations may utilize gravity, capillary action or other configurations or methodologies as will be recognized by those skilled in the art to additionally or alternatively assist in the introduction of moisture into the pressurized air at the humidification port 98. The moisture may be introduced as, for example, a spray or a vapor, or combinations thereof. Various nozzles, sprayers, orifices, jets, matrixes, meshes, membranes, wicking materials and similar fluid transfer devices may be provided at the humidification port 98 or otherwise as will be recognized by those skilled in the art to introduce the moisture into the pressurized air in the air delivery passage 28.

A control unit 38 may be provided to control one or more components of the positive airway pressure apparatus 10. The control unit 38 may be particularly adapted to control a blower 14. The control unit 38 may include one or more circuits and/or may include one or more microprocessors as well as a computer readable memory. The control unit 38 may be positioned within or on the housing 12, but may be otherwise positioned or located, including remotely, as will be recognized by those skilled in the art upon review of the present disclosure. The control unit 38 is typically configured to output one or more control signals to various components of the positive airway pressure apparatus 10. The control unit 38, in some aspects may be adapted to receive one or more signals from one or more components of the positive airway pressure apparatus 10. The control unit 38 may process or otherwise utilize the signals from the components of the positive airway pressure apparatus 10 in formulating the one or more control signals output to various components.

In one aspect, the control unit 38 may control the blower 14 in response to information including commands from the control interface 48. The control interface 48 includes one or more input devices, such as buttons or a touch-screen for example, to enter inputs for controlling features of the apparatus 10. The control interface 48 may also include a display and/or indicator lights to convey information about the operation of the apparatus 10 to a user or a health care professional. The control interface 48 may be in communication with the control unit 38 to transfer information to and/or from the control unit 38. In one aspect, the control interface 48 is in wired communication with the control unit 38. The control interface 48 may be secured, permanently or removably, to the housing 12 or may be otherwise positioned on components of the apparatus 10. The control interface 48 may also be configured as a remote control, either wired or wireless, as will be recognized by those skilled in the art upon review of the present disclosure. When configured as remote control, the control interface 48 typically includes a transmitter to transmit signals to a receiver associated with the control unit 38 and may include a receiver to receive signals from the control unit 38. The transmission may be RF, infrared, or other means. The control interface 48 may include one or more buttons, switches, touch screens, or other controls for controlling the blower 14 and associated components.

Figure 2:
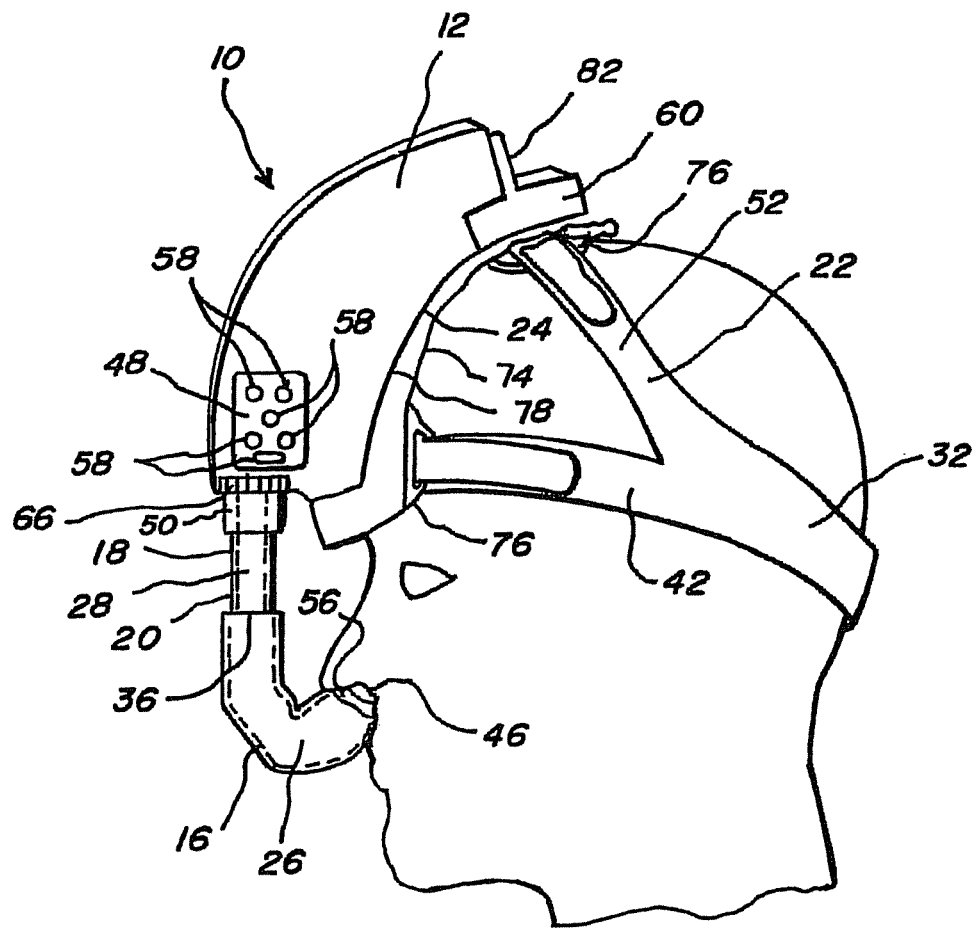
FIG. 2 illustrates a side view of an embodiment of another positive airway pressure apparatus in accordance with aspects of the present inventions secured to the head of a user.

As illustrated for exemplary purposes, FIGS. 1 to 5B particularly illustrate exemplary embodiments of positive airway pressure apparatus 10 in accordance with aspects of the present inventions. The illustrated embodiments include at least a housing 12, a blower 14 and a mask 16. The positive airway pressure apparatus 10 are configured to be secured medially on the heads of users with mounts 22. The mounts 22 generally are configured to extend about portions of the users' head to retain the housing 12 at a desired position on the head of a user and to permit the masks 16 to sealably engage the users' airways. As illustrated in FIGS. 1 and 3 for exemplary purposes, the apparatus 10 are generally configured to be positioned over the crown of user's head. As illustrated in FIG. 2 for exemplary purposes, the apparatus is generally configured to be positioned over the forehead of a user as well as over aspects of the crown of a user's head. The lower surfaces 24 of the housings 12 are generally shaped to conform to the portion of the head to which the housing 12 is secured. The masks 16 are secured to the housings 12 at a desired position relative to the housing 12 to facilitate the communication of pressurized air to the airways of a user. In the illustrated embodiments, the masks 16 are positioned below the housings 12 and may be positioned in front of the housings 12 as positioned on the head of a user. The illustrated embodiments generally cantilever the mask 16 from the housings 12 to position the masks 16 or porticins thereof about the airways of a user for exemplary purposes although those skilled in the art will recognize a wide range of configurations by which a mask 16 may be secured relative to the airways of a user.

As particularly illustrated in FIG. 1 for exemplary purposes, the mask 16 is secured relative to the housing 12 by a tube 18 that is integrally formed with the housing 12. The illustrated tube 18 is substantially rigid to function as a support 20 for maintaining the nares seals 56 of the mask 16 sealably engaged against the nares of a user during sleep. One or more adjustment members 66 may be provided on one or more of the housing 12, the mask 16, the air delivery tube 18, or the mask support 20. Such as for example, an adjustment member 66 in the form of a vertical adjustment member 102 may be provided to adjust the positioning of mask 16 up and down and a horizontal adjustment member 100 may be provided to adjust the closeness of the mask 16 or other structure to the face of a user. The housing 12 is configured with a base 30 and a cover 40. The housing 12 encloses a blower 14, not shown, within a housing interior 72. More particularly, the blower 14 is secured within the housing interior 72 defined between the cover 40 and the base 30. The base 30 defines a lower surface 24 configured with a downward curve 78 toward the front portion to conform to the shape of head between the forehead and crown. A mount 22 in the form of support bands 32 is secured to the base 30. The support bands 32 of the mount 22 include a circumferential band 42 and a first and a second stabilizing band 52. The circumferential band 42 is generally configured to extend about at least a portion of the circumference of a user's head. The housing 12 is secured to the circumferential band 42 at a location toward the anterior portion of the housing 12. An adjustable attachment may be provided on a posterior portion of the circumferential band 42. The first and second lateral stabilizing bands 52 are generally configured to stabilize the posterior portion of the base 30 of the housing 12 on the head of a user. The first and second lateral stabilizing bands 52 may each define at least a first end and a second end. The first and second lateral stabilizing bands 52 may be integral with or may be adjustably secured to the circumferential band 42 at their first ends. The second ends of each of the first and second lateral stabilizing bands 52 may be secured to a posterior portion of the base 30 of the housing 12. The cover 40 defines a housing air inlet 82 to communicate air into the housing interior 72. The housing air inlet 82 may be positioned on an upper surface of the housing 12 as shown or on other surfaces as one as will be recognized by those skilled in the art upon review of the present disclosure. The housing air inlet 82 may communicate air directly into a blower inlet 54 of the blower 14 within the housing 12. A control interface 48 is also positioned on an upper surface of the housing 12. As illustrated, the control interface 48 may include one or more controls 58. The controls 58 may be shaped, textured or otherwise configured to permit a user to differentiate between the controls 58 by touch. In certain aspects, this may include orientation of the controls 58, relative to one another and/or the housing, or sequence of the controls 58 as in a menu sequence when a touch screen is utilized. The blower 14 is secured within the housing 12 with the blower inlet 54 in fluid communication with the housing inlet 82 and the blower outlet 64 in fluid communication with the pressurized air passage 28 defined by the housing 12. The combination tube 18/mask support 20 extends forward and, then, downward from the housing 12 from which the first end of the combination tube 18/mask support 20 to position the second end of the combination tube 18/mask support 20 near or over the nose of a user when worn by the user. The mask passage 26 defined by mask 16 is in fluid communication with pressurized air passage 28 at the second end of the combination tube 18/mask support 20. As illustrated, the pressurized air passage 28 is in fluid communication with the mask passage 26 at the mask inlet 36. A first and a second mask seal 56 configured to permit the passage of pressurized air, define each of a first and second mask outlet 46, respectively, to sealably engage a nares of a user.

As particularly illustrated in FIG. 2 for exemplary purposes, the mask 16 is secured relative to the housing 12 by a tube 18 that is adjustably secured to the housing 12. The tube 18 also functions as a support 20 for the mask 16. The illustrated tube 18 is substantially rigid to function as a support 20 for maintaining the nares seals 56 of the mask 16 sealably engaged against the nares of a user during sleep. As illustrated, a generally tensile force may be applied between the mask 16 and the housing 12 to sealably engage the mask 16 within the nares of a user. The tube 18 as illustrated is vertically adjustable by a rotatable fitting 50 rotatably secured to the housing 12 and threadedly engaged with the tube 18 and permit adjustment along a substantially vertical axis. An adjustment member 66 allows adjustment of the position of the tube 18 and/or mask 16 to be made closer or further from the face as well as the angle relative to the plane of the face in order to accommodate differing anatomy. The housing 12 encloses a blower 14, not shown, within a housing interior 72. A battery 60 is also secured to the housing 12. The housing 12 defines a lower surface 24 configured with an approximately ninety (90) degree curve 78 to conform to the shape of the head between the forehead and crown. A pad 74 is secured to the lower surface 24 of the housing 12 to provide, in some embodiments, a more comfortable contact with a user's head. A mount 22 in the form of support bands 32 is secured through fittings 76 in the form of eyelets to the pad 74. The support bands 32 of the mount 22 include a circumferential band 42 and a first and a second stabilizing band 52. The circumferential band 42 is generally configured to extend about at least a portion of the circumference of a user's head. The pad 74 is secured to the circumferential band 42 at a location toward the anterior portion of the pad 74. Each of the ends of the support bands 32 may be provided with hook and loop type fasteners, for example, on opposing sides of the support bands 32 to among other thing permit the adjustability of length and/or tension when the support bands 32 are secured through fittings 76. The first and second lateral stabilizing bands 52 are generally configured to stabilize the posterior portion of the pad 74 on the head of a user. The first and second lateral stabilizing bands 52 may each define at least a first end and a second end. The first and second lateral stabilizing bands 52 may be integral with or may be adjustably secured to the circumferential band 42 at their first ends. The second ends of each of the first and second lateral stabilizing bands 52 may be secured to a posterior portion of the pad 74. The housing 12 defines a housing air inlet 82 to communicate air into the housing interior 72. The housing air inlet 82 is positioned on a substantially dorsal surface of the housing 12. The housing air inlet 72 may communicate air directly into a blower inlet 54 of the blower 14 secured within the housing 12. A control interface 48 is also positioned on a lateral surface of the housing 12. As illustrated, the control interface 48 may include one or more controls 58. The controls 58 may be shaped, textured or otherwise configured to permit a user to differentiate between the controls 58 by touch, orientation, or sequence as in a menu sequence with a touch screen approach. The blower 14 is secured within the housing 12 with the blower inlet 54 in fluid communication with the housing inlet 82 and the blower outlet 64 in fluid communication with the pressurized air passage 28 defined by the housing 12. The combination tube 18/mask support 20 extends downward from the housing 12 from which the first end of the combination tube 18/mask support 20 is adjustably secured to position the second end of the combination tube 18/mask support 20 and mask 16 at a desired location relative to the nose of a user. The mask passage 26 defined by mask 16 is in fluid communication with pressurized air passage 28 at the second end of the combination tube 18/mask support 20. As illustrated, the pressurized air passage 28 is in fluid communication with the mask passage 26 at the mask inlet 36. A first and a second mask seal 56 configured to permit the passage of pressurized air define each of a first and second mask outlet 46, respectively, to sealably engage a nares of a user.

As particularly illustrated in FIGS. 3 to 5B for exemplary purposes, the mask 16 is secured relative to the housing 12 by an air delivery tube 18 that is integrally formed with the housing 12. As illustrated in FIG. 3, the tube 18 is supported by substantially rigid mask supports 20 to maintain the mask 16 sealably engaged around the nose of a user during sleep. One or more adjustment members 66 may be provided on one or more of the housing 12, the mask 16, the air delivery tube 18, or the mask support 20. Such as for example, an adjustment member 66 in the form of a vertical adjustment member 102 may be provided to adjust the positioning of mask 16 up and down and a horizontal adjustment member 100 may be provided to adjust the closeness of the mask 16 or other structure to the face of a user. As illustrated in FIGS. 4A to 5B, the tube 18 is supported by substantially rigid mask supports 20 to maintain the nares seals 56 of the mask 16 sealably engaged against the nares of a user during sleep. The housing 12 encloses a blower 14, not shown, within a housing interior 72 defined by the housing 12. The housing 12 defines a lower surface 24 configured with a downward curve 78 toward the front portion to substantially conform to the shape of the head between the forehead and crown. A pad 74 is secured to the lower surface 24. A mount 22 in the form of support bands 32 is secured to the housing 12. The support bands 32 of the mount 22 include a circumferential band 42 and a first and a second stabilizing band 52. The circumferential band 42 is generally configured to extend about at least a portion of the circumference of a user's head. The housing 12 is secured to the circumferential band 42 at a location toward the anterior portion of the housing 12. An adjustable attachment may be provided on a posterior portion of the circumferential band 42. The first and second lateral stabilizing bands 52 are generally configured to stabilize the posterior portion of the housing 12 on the head of a user. The first and second lateral stabilizing bands 52 may each define at least a first end and a second end. The first and second lateral stabilizing bands 52 may be integral with or may be adjustably secured to the circumferential band 42 at their first ends. The second ends of each of the first and second lateral stabilizing bands 52 may be secured to a posterior portion of the housing 12. The housing 12 defines a housing air inlet 82 to communicate air into the housing interior 72. The housing air inlet 82 is positioned on an upper surface of the housing 12. The housing air inlet 82 may communicate air directly into a blower inlet 54 of the blower 14 within the housing 12. The blower 14 is secured within the housing 12 with the blower inlet 54 in fluid communication with the housing inlet 82 and the blower outlet 64 in fluid communication with the pressurized air passage 28 defined by the housing 12. The tube 18 and the mask support 20 extend forward and, then, downward from the housing 12 to which the first end of the tube 18 and the mask support 20 are secured. The mask support 20 is generally configured to position the mask 16 near or over the nose of a user when worn by the user. The mask passage 26 defined by mask 16 is in fluid communication with pressurized air passage 28 defined through the tube 18 at the second end of the tube 18. As illustrated, the pressurized air passage 28 is in fluid communication with the mask passage 26 at the mask inlet 36. A first and a second mask seal 56 configured to permit the passage of pressurized air define each of a first and second mask outlet 46, respectively, to sealably engage the face of a user about the nose as illustrated in FIG. 3 and within the nares of a user as illustrated in FIGS. 4A to 5B.

Figure 5A:
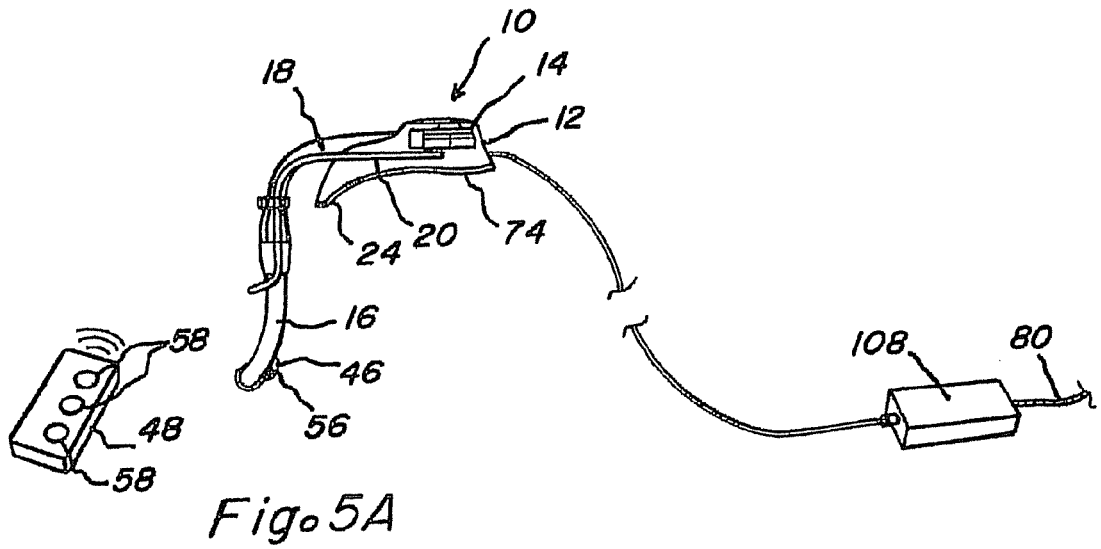
FIG. 5A illustrates a side view of an embodiment of a positive airway pressure apparatus including a remote control and a remote power supply in accordance with aspects of the present inventions.
Figure 5B:
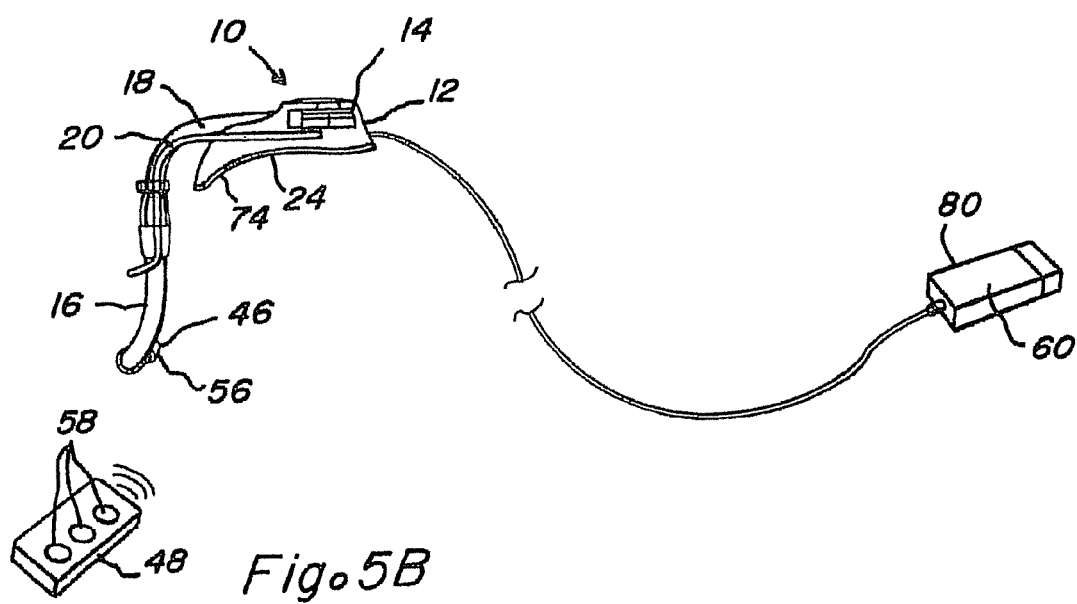
FIG. 5B illustrates a side view of an embodiment of a positive airway pressure apparatus similar to the embodiment of FIG. 5A including a remote control and a remote power supply in the form of a battery 60 in accordance with aspects of the present inventions.

As particularly illustrated in FIGS. 5A and 5B for exemplary purposes, the control interface 48 is provided as a remote control. The control interface 48 may include one or more controls 58. Further, the embodiment of FIG. 5A is shown with a remotely positionable DC converter 108 including a power cord extending to a power source 80 such as a household wall outlet. The embodiment of FIG. 5B is shown with a remotely positionable battery 60.

Figure 6:
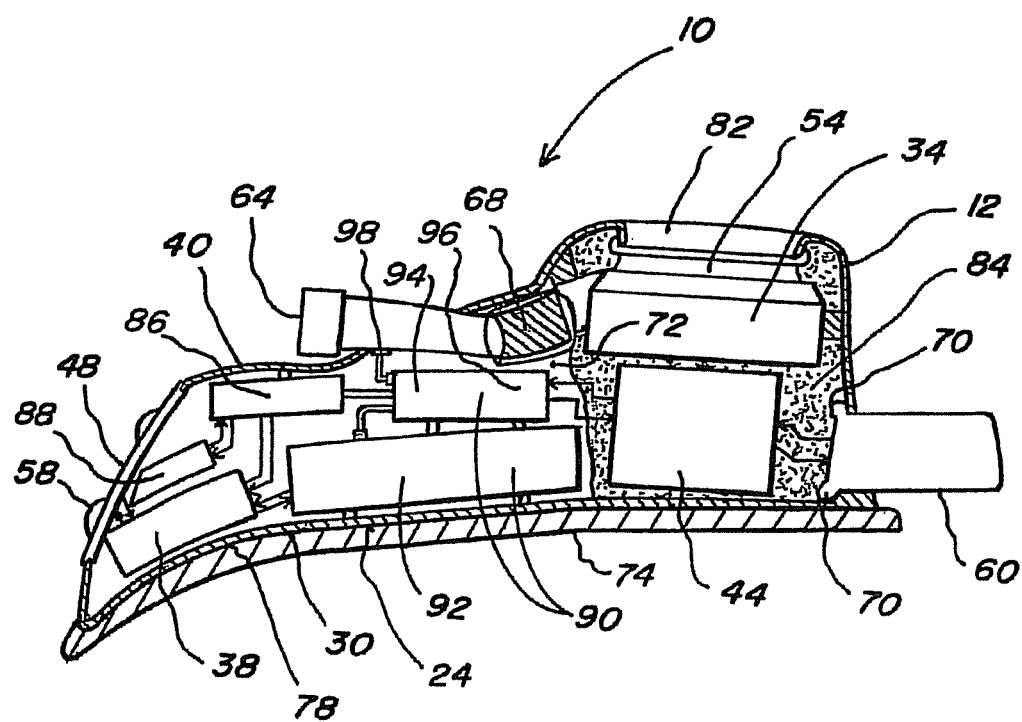
FIG. 6 illustrates a side view of an embodiment of a positive airway pressure apparatus in accordance with aspects of the present inventions with at least a portion of the housing in cross-section.

As particularly illustrated in FIG. 6 for exemplary purposes, the housing 12, shown in cross-section, may be configured to enclose and/or secure multiple components of the positive airway pressure apparatus 10 within a housing interior 72. As illustrated, the housing 12 may include a base 30 and a cover 40 which define the housing interior 72 as the open space between the base 30 and cover 40 when secured to one another. The lower surface 24 of base 30 may define a curve 78 to conform to aspects of the head of a user. A pad 74 may be secured directly to the lower surface 24 of the base 30. The pad 74 may conform to the curve 78 on the lower surface 24 of the base 30. The blower 14, the mask 16, the air delivery tube 18 (not shown), the mask support 20 (not shown), the humidifier 90 and other components of positive airway pressure apparatus 10 may be secured directly or indirectly to the housing 12 of positive airway pressure apparatus 10. As illustrated, the components are secured directly or indirectly to the base 30 or the cover 40 of the housing 12. The components are also in communication with one another as will be recognized by those skilled in the art upon review of the present disclosure. In certain aspects, the communication may be to transfer power, electrical or mechanical. In other aspects, the communication may be to communicate data. In other aspects, the communication may be to communicate mechanical forces. A battery 60 is removably secured within the rear portion of the housing 12 with at least a portion of the battery 60 extending into housing interior 72. The battery 60 is in electrical communication either directly or indirectly with each of the components which require electrical power for operation. The blower 14 may be secured within a rear portion of a base 30 of the housing 12 as well as to the cover of the housing 40. The blower motor 44 is secured to the base 30 and the air pressurizing assembly 34 is secured to the cover 40 for exemplary purposes. The blower motor 44 is connected to the air pressurizing assembly 34 to permit the blower motor 44 to confer power to the air pressurizing assembly 34. The blower motor 44 is in electrical communication with the battery 60. A sound deadening material 84 may be provided within at least a portion of the housing interior 72. In certain aspects, the sound deadening material 84 may be positioned about at least a portion of the blower 14. The sound deadening material 84 may be injection-molded foam. The control unit 38 is positioned in an anterior portion of the housing interior 72 and is secured to the base 30. The control unit 38 is in communication with blower motor 44 to provide control signals to the blower motor 44. The control unit 38 is in electrical communication with the battery 60. The control interface 48 is secured to an anterior portion of the cover 40 for exemplary purposes. The controls 58 of the control interface 48 are generally positioned and configured to permit a user to access the controls 58. The control interface 48 is in communication with the control unit 38 to at least provide control signals to the control unit 38. The control interface 48 is also in electrical communication with the battery 60. The control unit 38 is in communication with humidification pump 94 and/or humidification humidifier heater 96 to provide control signals to the humidification pump 94 and/or humidification humidifier heater 96. The humidification pump 94 and/or humidification humidifier heater 96 is in electrical communication with the battery 60. A noise cancellation speaker 86 and, in some aspects, a microphone 88 may be provided for purposes of noise cancellation. An output may be produced by the control unit 38 to generate a mitigating or cancelling waveform from the noise cancellation speaker 86 to reduce or eliminate the noise perceived by the user from the operation of the blower 14 and/or humidifier 90. In certain aspects, the microphone 88 may produce a signal indicative of the noise produced by the blower 14 and/or humidifier 90. The signal may be processed by the control unit 38 and an output produced by the control unit 38 to generate a mitigating or cancelling waveform from the noise cancellation speaker 86 to reduce or eliminate the noise perceived by the user from the operation of the blower 14 and/or humidifier 90.

Figure 7:
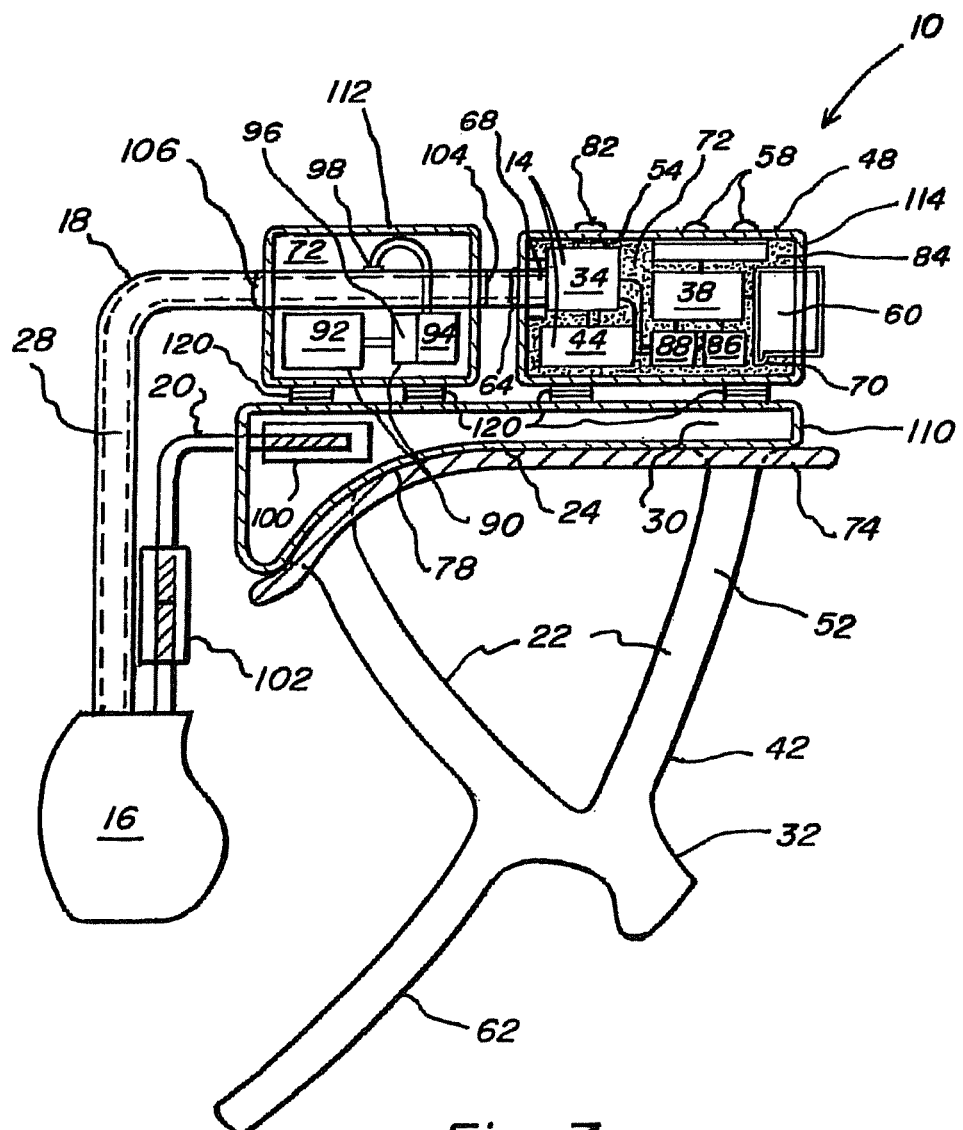
FIG. 7 illustrates a side view of another embodiment of a positive airway pressure apparatus in accordance with aspects of the present inventions with at least a portion of the housing in cross-section.

As particularly illustrated in FIG. 7 for exemplary purposes, the housing 12 of the respiratory therapy apparatus 10 may have a modular configuration. The modular configuration, as illustrated, includes the base 30 in the form of a head mounted platform module 110 to which the mask support 20 and the mount 22 are secured. One or more modules may be secured to the head mounted platform module 110. As illustrated, a humidification module 112 and a blower module 114 are secured to the head mounted platform module 110. The humidifier module 112 may be independent from blower module 114, as shown, or contained in a common module (not shown). Humidifier module 112 and blower module 114 may be connected together by one or more of screws, bolts, snaps, slots, or not physically attached together, but for the blower outlet 64 being in communication with the humidifier inlet 104 through pressurized the air passage 28. The lower surface 24 of the head mounted platform module 110 may define a curve 78 to conform to aspects of the head of a user. A pad 74 may be secured directly to the lower surface 24 of the head mounted platform module 110. The pad 74 may conform to the curve 78 on the lower surface 24 of the head mounted platform module 110. The humidification module 112 defines a housing interior 72 in which the humidifier 90 and other components may be secured. The blower module 114 defines a housing interior 72 in which for the blower 14, the control unit 38, and the battery 60 are secured for exemplary purposes and in which other components may be secured. The humidification module 112 and the blower module 114 may be removably attached to the head mount platform module 110. The humidification module 112 and/or the blower module 114 may be attached to the head mount platform module 110, one another or to other components with one or more attachments 120. The attachments 120 may be in the form of screws, bolts, snaps, slots, sleeves, hook and loop type fasteners, various fittings and couplers or other engagement mechanisms as will be recognized by those skilled in the art upon review of the present disclosure. The attachments 120 may further include dampers or may function as dampers to mitigate or prevent the transmission of vibration between modules. As illustrated, the air delivery tube 18 is secured in fluid communication with the humidifier outlet 106 and the blower outlet 64 is in fluid communication with the humidifier inlet 104 to form a pressurized air passage 28 extending between the blower 14 and the mask 16. To form the pressurized air passage 28, the various components may in various fittings and/or couplers to permit the sealed engagement of abutting portions of modules 112, 114, air delivery tube 18, or other tubing or components of the positive airway pressure apparatus that may be associated with defining the pressurized air passage 28. A battery 60 may reside within blower module 114 as illustrated, may be associated with other modules, may be provided in an independent battery module, or may be provided remotely as will be recognized by those skilled in the art upon review of the present disclosure. A sound deadening material 84 may be provided within at least a portion of the housing interior 72 of at least one of the blower module 114 and the humidifier module 112. The sound deadening material 84 may be injection-molded foam. In certain aspects, the sound deadening material 84 may be positioned about at least a portion of the blower 14.

Figure 8:
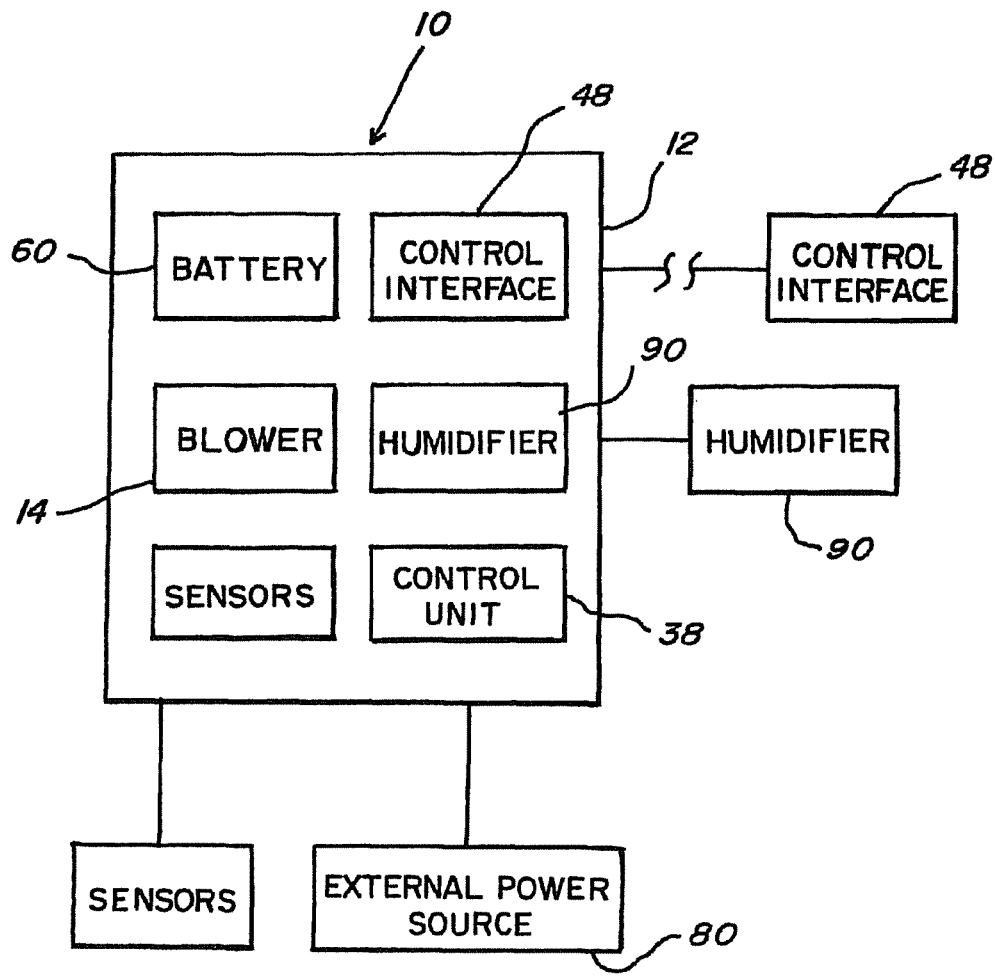
FIG. 8 is a diagram illustrating exemplary components of positive airway pressure apparatus in accordance with aspects of the present inventions.

As illustrated in FIG. 8 for exemplary purposes, a variety of components may be positioned secured to or remote from housing 12 in accordance with aspects of the present inventions. As illustrated, blower 14, control unit 38, control interface 48, battery 60, humidifier 90, and various sensors may be secured to housing 12. Also, control interface 48, battery 60, humidifier 90, and various sensors or components thereof may be remote from housing 12. Those skilled in the art will recognize additional components that may be included with positive airway pressure apparatus 10 that may be secured to or remote from the housing 12 upon review of the present disclosure which are in accordance with aspects of the present inventions.

To use a positive airway pressure apparatus 10 in accordance with the present inventions, a user may secure the housing 12, the blower 14 and the mask 16 to his-or-her head. The mask 16 is positioned in communication with the airways of the user. The positive airway pressure apparatus 10 may be configured to administer one or more positive airway pressure therapies, including: continuous positive airway pressure therapy (CPAP), bilevel positive airway pressure therapy (BPAP), automatic positive airway pressure therapy (auto- PAP), proportional positive airway pressure therapy (PPAP), non-invasive ventilation and/or other positive airway pressure therapies as will be recognized by those skilled in the art upon review of this disclosure. In certain aspects, the mask 16 may be sealingly secured over one or more aspects of the user's face. The seal is typically sufficient to prevent substantial leaking of pressurized air from the interface of the mask 16 and the user's anatomy such that effective positive airway pressure therapy can be administered to the user. The user then initiates the positive airway pressure therapy. The pressure may be initiated by hitting a start button secured to the housing 12 or on a remote control or otherwise as will be recognized by those skilled in the art upon review of the present disclosure. The pressure in the user's airways is then increased to a therapeutically efficacious level. Typically, this is between 4 and 20 cm of water. In certain aspects, the pressure may increase to therapeutic levels immediately upon hitting the start button. In other aspects, the pressure may increase from an initially low or non-therapeutic level to therapeutic levels after a delay. The pressure may be increased gradually or may be immediately increased from atmospheric or slightly higher pressure to a therapeutic pressure. In certain therapies, the pressure may be modulated within or between breath cycles and/or in accordance with the sleep cycle of a user as will be recognized by those skilled in the art upon review of the present disclosure. This modulation may be in response to input from sensors into the control unit of the positive airway pressure apparatus 10.

The foregoing discussion discloses and describes merely exemplary embodiments of the present invention. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. An apparatus for providing positive airway pressure therapy to a user, the apparatus comprising:
   a blower configured to generate pressurized air;
   a mask connected to an output of the blower, the mask configured to deliver the pressurized air from the blower to an airway of the user; and
   a base operatively attached to the blower, wherein the base is configured to attach to a head of the user in order to secure the blower to the head, the base comprising a surface configured to conform to a shape of a portion of the head to which the base is intended to attach.

2. The apparatus of claim 1, further comprising a cover securable to the base such that the cover and base form at least part of a housing, the housing defining a housing interior configured to at least partially enclose the blower.

3. The apparatus of claim 1, wherein the mask is selected from the group consisting of a face mask, a nose mask, a pair of nares seals, and a mouthpiece.

4. The apparatus of claim 1, wherein the blower comprises an air bearing.

5. The apparatus of claim 1, wherein the surface configured to conform to the shape of a portion of the head comprises a compressible pad.

6. The apparatus of claim 1, wherein the base is configured as a platform module and the blower is configured as a blower module securable to the platform module.

7. The apparatus of claim 6, further comprising a humidification module configured to secure to the platform module.

8. The apparatus of claim 1, further comprising a DC power converter and a supply cord configured for delivering DC power to the blower.

9. The apparatus of claim 1, further comprising a battery in electrical communication with the blower.

10. The apparatus of claim 1, further comprising one or more noise absorption baffles or resonators in communication with an outlet of the blower to at least mitigate a sound produced by at least the blower.

11. The apparatus of claim 1, further comprising a control unit in communication with a noise cancellation speaker, the control unit configured to provide a control unit output to the noise cancellation speaker to produce a waveform to at least mitigate a sound produced by at least the blower.

12. The apparatus of claim 11, further comprising a microphone in communication with the control unit, the microphone configured to provide a microphone output indicative of the sound produced by at least the blower, wherein the control unit is configured to process the microphone output and generate the control unit output to the noise cancellation speaker.

13. A method for providing positive airway pressure therapy to a user, the method comprising:
   securing a mask to the user, the mask operable to communicate with an air passageway of the user;
   securing a housing containing a blower to a head of the user, the blower configured to deliver pressurized air at a pressure of at least between 4-20 cm of water to the mask, wherein the housing comprises a surface configured to conform to a shape of a portion of the head to which the housing is secured; and
   delivering the pressurized air from the blower to the mask.

14. The method of claim 13, wherein delivering the pressurized air from the blower to the mask comprises connecting an outlet of the blower to an inlet of the mask with a delivery tube.

15. The method of claim 13, wherein securing the housing to the head comprises securing the housing to the head with one or more mounts selected from the group consisting of a flexible cap, one or more rigid or semi rigid members, and one or more support bands.

16. The method of claim 13, wherein securing the mask to the user comprises securing the mask with a mask support attached to the housing.

17. The method of claim 13, further comprising connecting the housing to an external source of electrical power.

18. The method of claim 13, further comprising connecting the blower to a battery.

19. The method of claim 13, further comprising: securing a humidifier to the head of the user; and humidifying the pressurized air with the humidifier.

20. An apparatus for providing positive airway pressure therapy to a user, the apparatus comprising:
   a housing adapted to be secured on one or both of a crown and a forehead of a user, the housing comprising a base defining a surface configured to conform to a shape of one or both of the crown and the forehead;
   a blower configured to deliver pressurized air at a pressure between 4-20 cm of water, the blower secured within the housing, the blower defining a blower inlet and a blower outlet; and
   a mask defining a mask inlet and a mask outlet, wherein the mask inlet is in fluid communication with the blower outlet, and wherein the mask outlet is configured to communicate the pressurized air to an airway of the user.

* * * * *